United States Patent [19]
Vincent et al.

[11] Patent Number: 5,195,112
[45] Date of Patent: * Mar. 16, 1993

[54] X-RAY COMPUTER TOMOGRAPHY SYSTEM

[75] Inventors: Paul Vincent, Karlsruhe; Günther Laukien, Rheinstetten; Arne Kasten, Karlsruhe, all of Fed. Rep. of Germany

[73] Assignee: Bruker Analytic, Fed. Rep. of Germany

[*] Notice: The portion of the term of this patent subsequent to Mar. 2, 2010 has been disclaimed.

[21] Appl. No.: 695,517

[22] Filed: May 3, 1991

[30] Foreign Application Priority Data

May 11, 1990 [DE] Fed. Rep. of Germany ....... 4015105

[51] Int. Cl.⁵ ............................................... A61B 6/00
[52] U.S. Cl. ......................................... 378/10; 378/12; 378/134; 378/137
[58] Field of Search ..................... 378/4, 9, 10, 11, 12, 378/13, 14, 15, 16, 19, 62, 121, 124, 134, 136, 137, 138

[56] References Cited

U.S. PATENT DOCUMENTS

| | | | |
|---|---|---|---|
| 4,031,395 | 6/1977 | LeMay | 378/10 |
| 4,158,142 | 6/1979 | Haimson . | |
| 4,289,969 | 9/1981 | Cooperstein et al. | 378/9 |
| 4,352,021 | 9/1982 | Boyd et al. . | |
| 4,592,079 | 5/1986 | Sohval et al. | 378/9 |
| 4,754,468 | 6/1988 | Mori | 378/19 |

FOREIGN PATENT DOCUMENTS

| | | |
|---|---|---|
| 264055A1 | 3/1977 | Fed. Rep. of Germany . |
| 2650237 | 5/1978 | Fed. Rep. of Germany . |
| 2821870 | 5/1978 | Fed. Rep. of Germany . |
| 2714759 | 10/1978 | Fed. Rep. of Germany . |
| 2723462 | 12/1978 | Fed. Rep. of Germany . |
| 83904786 | 3/1984 | Fed. Rep. of Germany . |
| 2034149 | 5/1980 | United Kingdom . |

OTHER PUBLICATIONS

IEEE Trans. Nucl. Sci. NS-26 No. 2 p. 2713 (Robb et al.), The DSR: A High-Speed Three-Dimensional X-Ray Computed Tomography System for Dynamic Spatial Reconstruction of the Heart and Circulation, Apr. 1979.

*Primary Examiner*—David P. Porta
*Attorney, Agent, or Firm*—Wolf, Greenfield & Sacks

[57] ABSTRACT

An X-ray computer tomography system with a stationary ring anode and a plurality of stationary electron sources for the construction of fast scan images from the inside of an object is improved in such a way that there is free access from both sides of the scan region, that the gantry unit can be tilted, and that the image quality which can be achieved is comparable to that of conventional tomography systems with mechanical motion of the anode. A plurality of electron sources are configured in proximity to the ring anode on a stationary ring, with each source being capable of sweeping its respective electron beam over a portion of the anode ring.

35 Claims, 7 Drawing Sheets

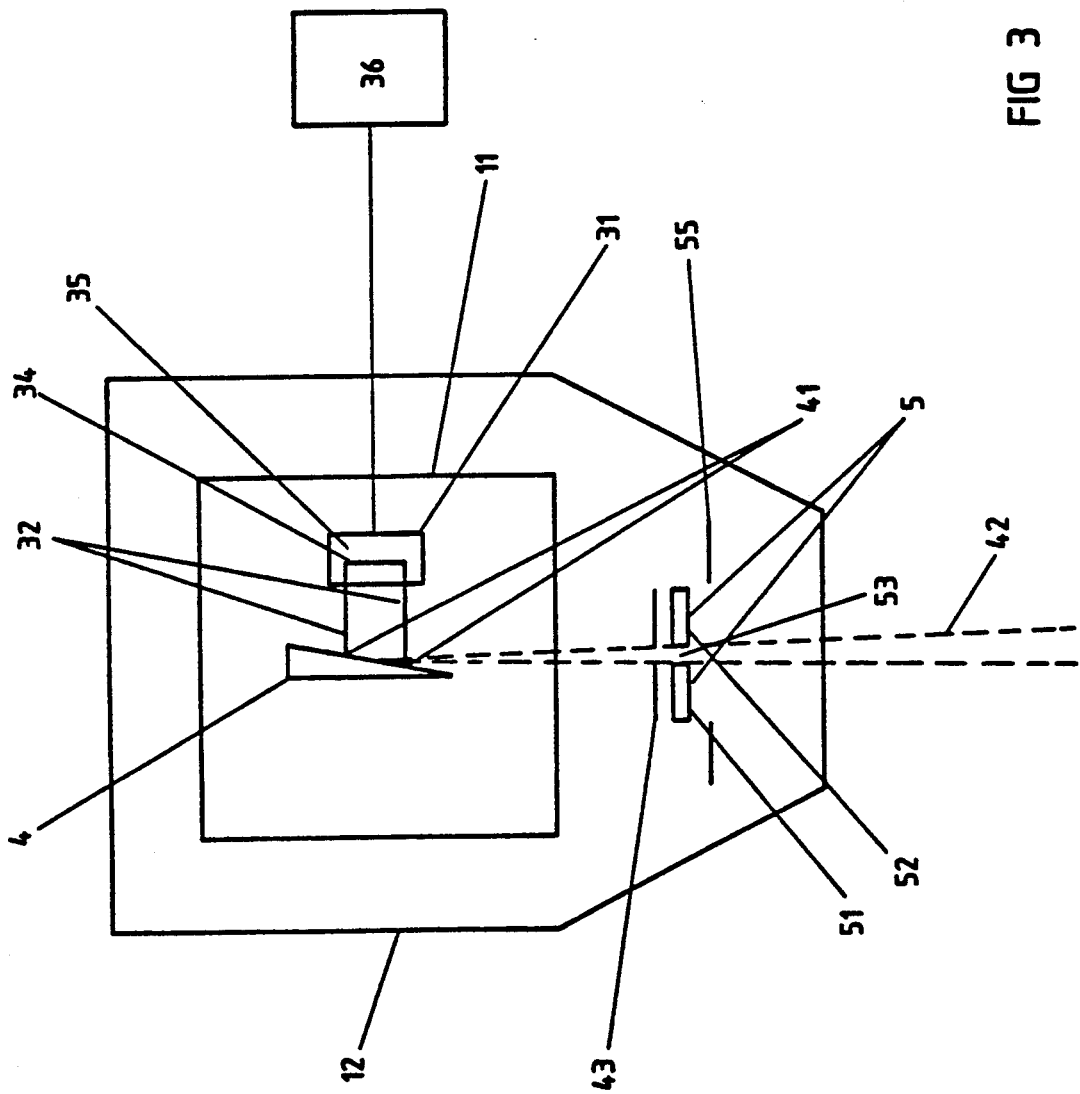

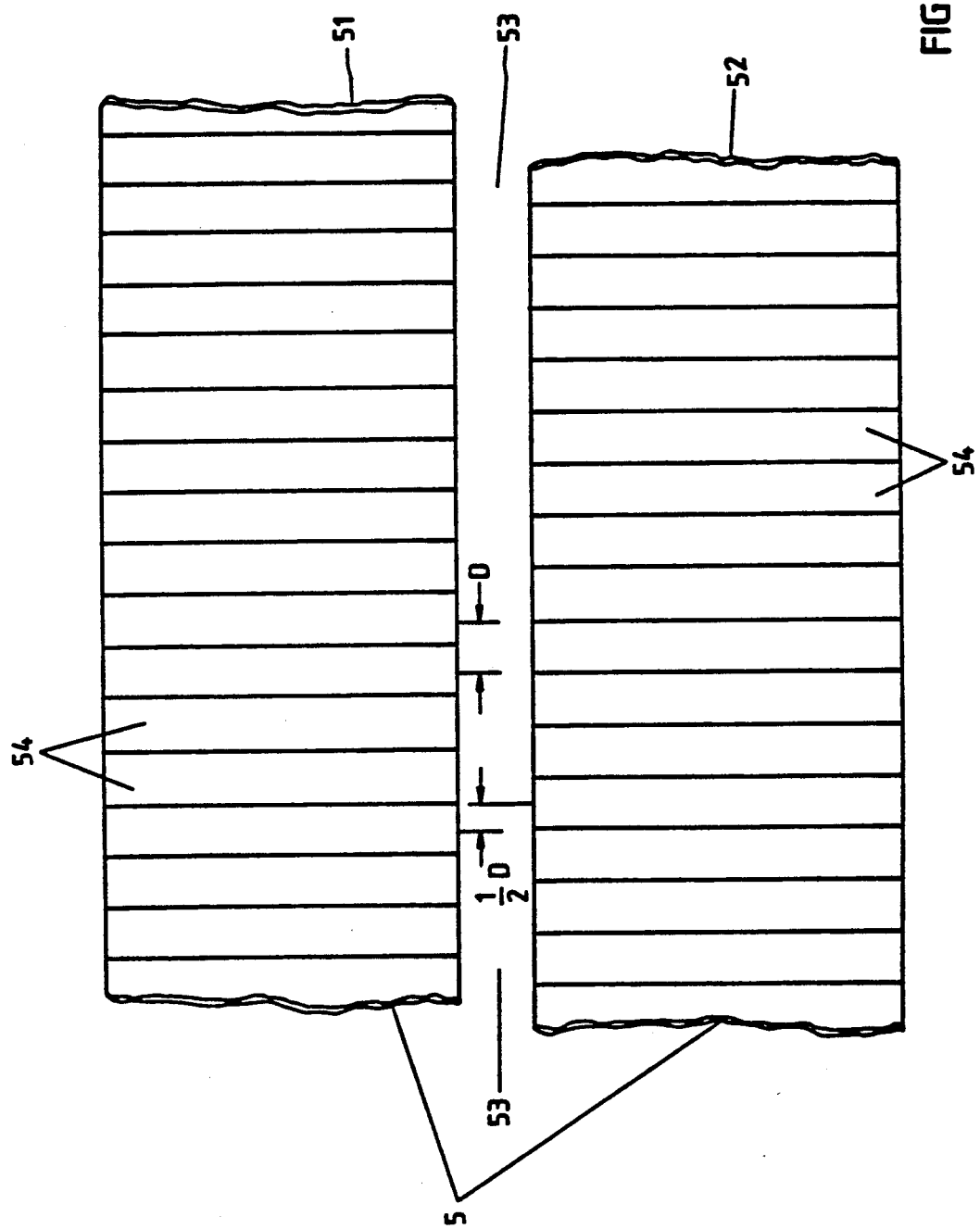

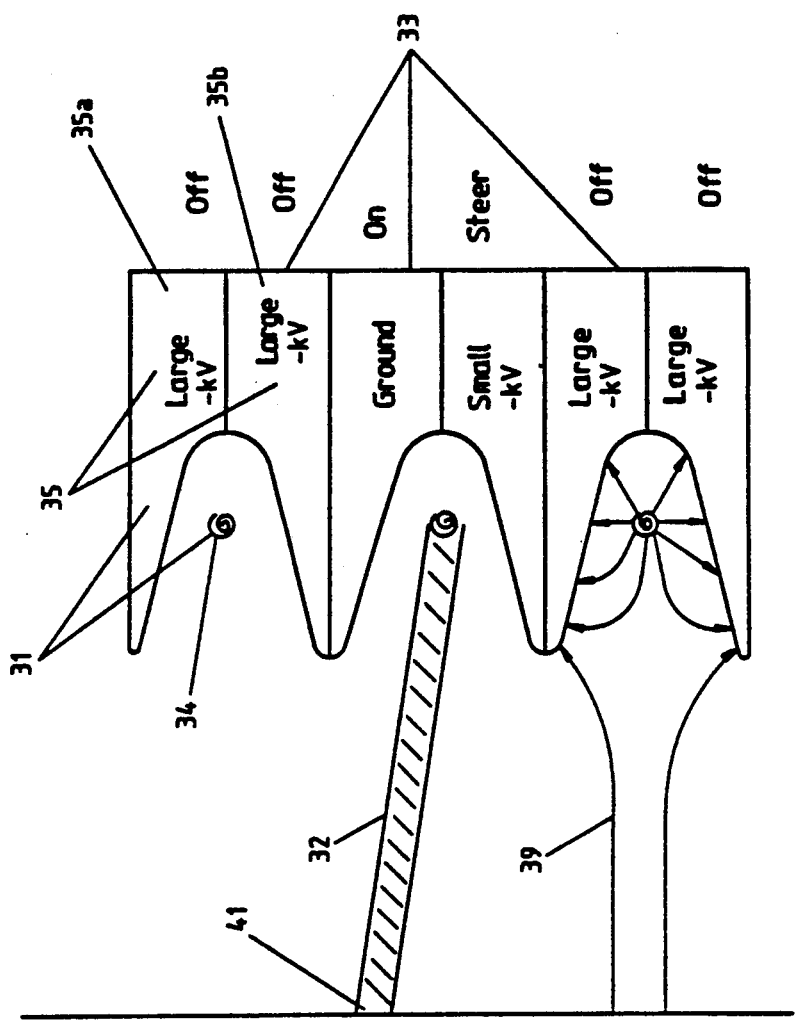
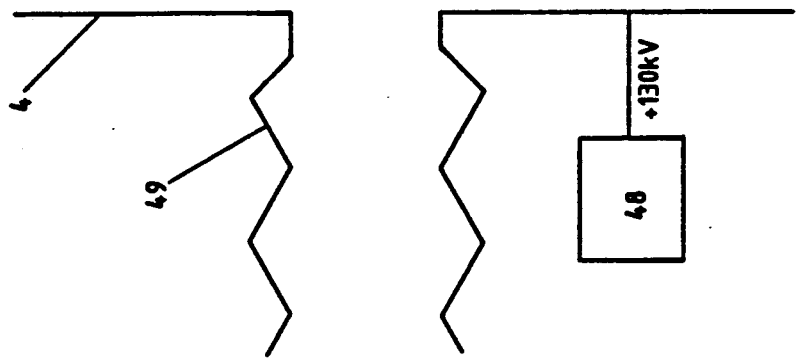
FIG 5

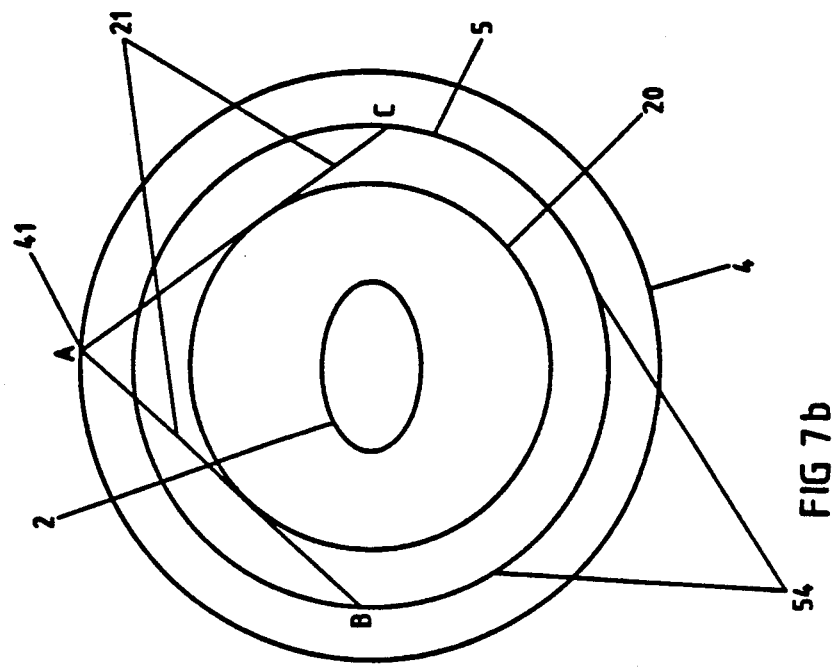
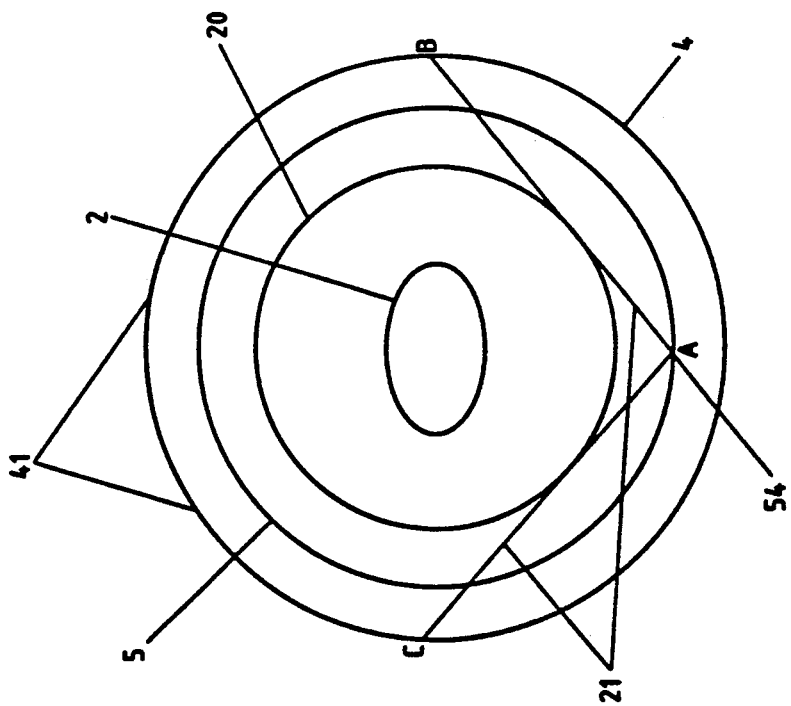

X-RAY COMPUTER TOMOGRAPHY SYSTEM

FIELD OF THE INVENTION

The invention concerns an X-ray computer tomography scanner for the generation of slice images from the inside of an object which exhibits a plurality of stationary electron sources and a stationary anode ring as well as a method for the operation of such a system. X-ray computer tomographs with a plurality of electron sources are known in the art from the German patent publication DE 27 14 759 B2.

DESCRIPTION OF THE PRIOR ART

DE 27 14 759 B2 discloses an x-ray computer tomography system which exhibits a stationary ring anode and a ring detector array of smaller diameter. A ring of electron sources is positioned in close proximity to the anode. In the embodiment of the invention, there are 360 such sources equally spaced around a circle in close proximity to the anode and the sources exhibit preheated filaments. The sources are sequentially activated by switching in a suitable high voltage between the anode and an individual source such that an electron beam is successively formed between each activated source and the portion of the anode in direct proximity to said source so that an x-ray beam is formed and emerges from the point where the electron beam strikes the anode, i.e. the focal spot. In the embodiment, the sources are sequentially switched on and off so that the focal spot moves stepwise around the anode in discreet steps of 1° until a full 360 degree scan is effected.

DE 27 14 759 exhibits mechanical motion of both an x-ray beam collimator and the detector during the course of a scan. The collimator rotates along with the focal spot during the course of a scan in such a way that it is aligned with the x-ray beam emerging from the focal spot. The detector consists of detector elements which are gimbal mounted in such a way that those detector elements which are required to detect the x-rays emanating from a given focal spot of a given electron source are mechanically swung in and out of the scan plane as focal spot and collimator rotate around the object being scanned.

DE 27 14 759 discloses an x-ray source which produces 360 stationary focal spots at discrete separated locations around the anode ring. This source exhibits short anode lifetime and reduced image quality compared to that of conventional scanners with mechanically rotating x-ray sources.

The fact that the focal spots are stationary with respect to the anode surface in DE 27 14 759 means that each electron beam always strikes the same location on the anode. Due to this uneven localized heat load distribution of small focal spots separated by distances which are large compared to the focal spot sizes, the anode is subject to localized expansion stresses which, in turn, will limit its overall lifetime. In addition, only a fraction of the available anode surface is actually used to produce x-rays, further reducing the overall lifetime of the anode. The large local heating at the position of the focal spot limits the maximum allowable electron beam intensity and, thereby the associated x-ray yield which, in turn, limits the detector signal to noise ratios and the overall low contrast resolution of the imaging system. If one attempts to improve the low contrast resolution by increasing the x-ray yield, one is compelled to increase the size of the focal spot and, thereby, the effective used portion of the anode which, in turn, causes a reduction in the spatial or high contrast resolution. Furthermore, the number of view angles is restricted to being equal to the number of sources, i.e. 360. However, larger numbers of view angles per scan, by way of example 1000, are necessary not only for spatial resolution but also for the reduction of imaging artifacts due to inconsistent or incorrect data. Increasing the number of view angles to, by way of example, 1000 in the apparatus according to DE 27 14 759 would require nearly a tripling in the number of electron sources with an associated increase in technical complication and expense.

Furthermore, DE 27 14 759 exhibits the disadvantages associated with scanners requiring mechanical motion to effect a scan.

Mechanically moving tomography systems are subject to additional noise due to mechanical vibration (microphonics) and associated degraded image quality, as well as limited reliability due to required maintenance associated with mechanically moving parts. Moreover, mechanically rotating scanners are usually limited to scan times of about 1 second for a complete 360 degree scan. Therefore, imaging of quickly moving objects such as the beating human heart is not possible. In addition, imaging artifacts due to patient motion during the course of the scan occur.

The scanner disclosed in DE 27 14 759 exhibits a time resolution which is a fixed fraction of the total scan time.

Since the collimator mechanically rotates in such a way that it is aligned with the x-ray beam emerging from the focal spot, the scanner must be operated in such a way that neighboring x-ray sources are sequentially switched on and off, i.e. it is not possible to scan sequentially with widely separated sources. In this manner one obtains a series of measurements of the x-ray radiation transmitted through the object at various view angles about the object. Since a continuous scan of at least 180 degrees is normally necessary for image reconstruction, this system has a minimal time resolution given by the time required by the source to transcribe 180 degrees. Since the source moves along spatially sequential positions, this minimum time resolution is bounded by a fixed fraction of the total scan time with this fixed fraction usually corresponding to at least one half for a total 360° scan. Therefore, the minimum time resolution is a fixed fraction of the total scan time, and no adjustable compromise between spatial, low contrast, and minimum time resolution through the selection of the number of view angles to be analyzed can be made.

An X-ray computer tomograph wherein, for a given scan time, the minimum time is not bounded from below by a fixed fraction of the scan time is described by Robb et al. in IEEE Trans. Nucl. Sci. Vol. NS-26 No. 2, 1979, pages 2713 to 2717. In this tomograph 28 individual standard X-ray tubes are attached to a mechanically rotating ring at equal separations with respect to each other, whereby the angular separation between the first and the last tube corresponds to approximately 180 degrees. By rapid sequential pulsing of each tube, a set of 28 view angles can be measured within a time interval which is small compared to the time taken by the ring to mechanically rotate through the angular separation between two adjacent tubes. By repetitively pulsing the 28 tubes while the ring rotates, view angles at angular values intermediate between those of the first set of the 28 measurements can be obtained. Since each set of 28 measurements describes 180 degrees, one set is sufficient for image reconstruction. As soon as more sets are included in the image reconstruction process, the spatial resolution and the low contrast resolution are improved. Therefore, the minimum time resolution of this system is equal to the time necessary to acquire one set of 28 tube pulses. This minimum time is, in general, not a fix fraction of the total scan time, rather it is adjustable according to whether or not time resolution, spatial resolution or low contrast resolution are considered to be more important.

The scanner of Robb et al exhibits mechanical motion of the x-ray source array and therefore all the associated disadvantages which have already been described in detail above.

Due to the above mentioned deficiencies in X-ray computer tomographs exhibiting a plurality of x-ray sources, it is the purpose of the present invention to improve an X-ray computer tomography system for the production of image slices through an object, which exhibits a plurality of electron sources arranged in proximity to a stationary anode with means for accelerating electrons emitted from the electron source towards the anode ring such that the electrons form an electron beam which collides with the anode ring at focal spots to emit X-ray radiation, and with a full or partial X-ray detector ring, in such a way that mechanical motion of the x-ray and detector is avoided during the course of a scan so that fast scan speeds are possible but with image quality comparable to that of conventional tomography systems.

BRIEF SUMMARY OF THE INVENTION

The purpose of the invention is achieved in that, the electron sources exhibit means for electromagnetically sweeping their corresponding focal spots over respective portions of the anode surface during the course of the scan.

In this manner the underlying purpose of the invention is fully achieved. The fact that the focal spots can be swept over the surface of the anode during the course of the scan allows for optimal use of the anode surface with decreased localized heat loading and thereby, for the use of small focal spots and large electron beam currents with associated good low and high contrast resolution. Furthermore, the number of view angles is not restricted to being equal to the number of electron sources resulting in the capability for a large number of view angles and associated further improvements in high contrast resolution and resistance to imaging artifacts. The fact that the individual electron beams are swept electromagnetically rather mechanically during the course of the scan means that mechanical motion during the course of the scan is completely avoided thereby allowing for very high scan speeds.

The invention allows computer tomography scans to be executed without moving either the X-ray source or the detector configuration. In this manner, scan times of 50 ms or less, are possible for a complete 360 degree scan. The tomograph in accordance with the invention also exhibits some mechanical motion to the extent that, by way of example, the slice thickness is adjusted by adjusting a collimator ring. This should, however, not be confused with the angular rotation of the X-ray source and associated x-ray collimator or the detector configuration during the course of a scan.

In a preferred embodiment of the invention there are 250 such electron sources at equal angular intervals about a circular ring the radius of which is approximately 400 mm, whereby the electron sources are approximately at ground potential and the anode lies approximately at +100 kV to +150 kV, preferentially, approximately +130 kV. The electron sources and the anode ring are located in a common vacuum vessel and the electron sources are individually controllable in order to emit electron beams in a predetermined time sequence.

The electrons emanating from the electron sources are focused into a beam which strikes the anode at a focal spot and produces X-ray radiation (largely Bremsstrahlung) from which an X-ray fan beam is collimated. In a preferred embodiment of the invention X-ray radiation coming from the focal spot which has penetrated through the object is detected in a complete 360 degree X-ray detector ring whereby the detector ring is comprised of two adjacent parallel partial rings of equal radius. The partial rings are displaced in a direction largely perpendicular to the scan slice so that a ring-shaped gap is formed between them and the detector ring and the anode ring are coaxial and largely coplanar to each other so that the two rings define a largely planar scan region wherein the fan beam is located. The gap between the two detector partial rings is large enough to allow the entire fan beam with the desired slice thickness to pass through but small enough to permit most of the radiation penetrating through the object to also be detected, that is to say, to strike the detector ring. This configuration is the object of a parallel patent application filed on the same date entitled "X-Ray Computer Tomography System with Split Detector Ring" by inventors P. Vincent, G. Laukien, and A. Kasten and corresponding to German patent application P 40 15 180.8-33, and the contents disclosed in this application is, through this reference, incorporated into the contents disclosed in the present application.

In a particularly preferred embodiment, the radius of the detector ring is approximately 330 mm and each partial ring contains 1200 individual detector elements which are suited for the detection of X-ray radiation emanating from the focal spot on the anode ring. Other embodiments with elliptical instead of circular detector and anode rings are possible.

The slice thickness of the scan is adjustable through a relative displacement of the two detector partial rings in a direction largely perpendicular to the scan plane, such that each detector partial ring is displaced equally but in opposite directions in order to change the width of the detector ring gap. The geometry of the system is so arranged that the relationship $Rd/Rf = (wd - g)/(wd + g)$ is approximately satisfied, whereby g is the width of the gap between the detector partial rings, wd the width of the fan beam after penetration of the object at the detector ring location across from the focal spot, Rd the detector ring radius and Rf the radius of the position of the focal spot on the anode ring. In a particularly preferred embodiment of the invention $Rd = 330$ mm, $Rf = 400$ mm, and $g/wd = 0.1$.

In an embodiment of the invention, each electron source consists of a heated filament for the production of electrons and a hollow cathode. Thereby, in a particularly preferred embodiment, the hollow cathode is subdivided into two or more segments which are electrically isolated from each other. By applying, relative to the filament, a negative voltage of adjustable strength of up to several kV on one or more of the hollow cathode segments, one is able to switch on and off, focus and steer the electron beam emitted by the cathode. The shape of the hollow cathode and its separation from the anode are so chosen that the electrons emitted from each respective filament are focused into a beam which is accelerated towards the anode and collides with it at a focal spot. Procedures for calculation of electron orbits for a given potential distribution taking into consideration space charge effects are known to one of average skill in the art. By sequentially pulsing (in general, controlling) the voltage on the hollow cathode segments, it is possible to generate a ring source of X-ray radiation such that any given segment of the ring can be caused to emit X-rays in a predetermined time sequence. In place of or in addition to the segmentation of the hollow cathode, it is also possible to achieve a (partial) continuous potential distribution by giving portions of the surface electrical resistance.

In a preferred embodiment, the detector elements of the two partial rings are rotated with respect to each other by an angle which approximately corresponds to half the angular width of an individual detector element. During the course of a scan, the data from each individual one of the, in total, 2400 detector elements is registered and processed. Additional detectors for monitoring scattering and changes in the X-ray intensity are introduced outside of the scan slice in the vicinity of the detector ring.

The small radius of the preferred embodiment of the invention leads to a strong increase in the X-ray intensity for a given slice thickness, scan-time, and field of view which, in turn, leads to an improved signal to noise ratio in the detectors and to improved low contrast resolution. In addition, the small detector ring radius leads to, for a given total number of individual detector elements, a reduction in a size of the individual detector elements and, thereby, to improved spatial resolution. The splitting of the detector configuration into two partial rings separated by a narrow gap facilitates coplanarity of the X-ray source ring (anode) and the detector ring and allows scans over a complete 360°, which, in turn, reduces partial volume and other artifacts. The utilization of a plurality of individually controllable electron sources without mechanical rotation allows the angular position of the X-ray source to be selected in any desired sequence which, in turn, for each given scan, implies that the minimum time resolution is selectable over a wide range. Therefore, the minimum time resolution is not a fixed fraction of the scan time, but rather is selected by the user, with the user weighing the relative importance of time, spatial, and low contrast resolution.

By sequentially switching on and off electron sources which have wide angular separations from each other, by way of example, approximately 120°, it is possible to sequentially illuminate detector elements which were largely unaffected by the previous firing. In particular, if the repetition rate is on the order of the afterglow time of the detector elements one can largely avoid temporal cross talk from remnants of the previous scintillation excitation.

The X-ray computer tomography system according to the invention can be advantageously operated in the two modes described below. In a first operation mode each detector element generates one view angle in that one repetitively registers, digitalises, and stores the X-ray intensity incident upon this detector element during the time period when X-ray radiation emanating from the focal spot and reaching the detector sweeps across the desired field of view. In this operation mode the focal spot moves continuously or quasi-continuously along an arc around the anode ring (continuous focal spot).

In a second preferred operation mode, a view angle is generated for every position of the focal spot in that one reads out all detector elements in the region of the fan beam overlapping the desired field of view. In this second operation mode it is not necessary for the focal spot to continuously move further along the anode ring after the time interval during which the detector elements are read out, rather, it can discontinuously jump from one position on the anode to the next, with these positions being far apart from each other.

In both operation modes it is possible to read out and to analyze the data from the, preferentially, approximately 2400 detector elements of the two detector rings in such a manner that two directly adjacent image slices are reconstructed such that, for each slice, the data from one detector partial ring is analyzed (two slice analysis).

Alternatively, the data from all of the 2400 detectors can be utilized to reconstruct a common image slice of twice the slice thickness with, however, in general, an improved spatial resolution in the slice (one slice analysis).

The one slice analysis advantageously utilizes the fact that one detector partial ring is rotated with respect to the other by approximately one half of a detector element width (more specifically: by half of the arc length corresponding to the circumference of the detector ring divided by the number of detectors), so that a doubling of either the number of view angles per scan or the number of data points per view angle compared to the two slice analysis occurs and, thereby, an improved spatial resolution within the slice (however with a doubled slice thickness) is achieved.

In a particularly preferred first operation mode of a computer tomography scanner according to the invention, the electron beam focal spot describes an approximately 400 mm radius continuous arc of 360° about the anode ring within 50 ms and each detector element of the 300 mm radius detector ring is read out 1200 times during the time interval in which said element is located within the region of the fan beam overlapping the desired field of view. In this operation mode a field of view of 500 mm diameter requires a sampling time of approximately 20 microseconds. If the diameter of the focal spot on the anode is approximately 1 mm then, in this operation mode spatial resolutions of approximately 1 mm can be achieved with a two slice analysis.

In the first operation mode all electron sources are switched off immediately preceding the execution of a scan, that is to say a negative voltage of several kilovolts with respect to the filament is applied to all hollow cathode segments of all electron sources with heated filaments. At the beginning of the scan the negative voltage of at least one hollow cathode segment of a first electron source is reduced to approximately the potential of the filament (in general, ground potential). Preferentially, this also occurs with the second hollow cathode segment of this first electron source. Through this measure the electron beam of the first source is switched on. Through adjustment of the small remaining voltage on the hollow cathode segments, the beam is focused and steered in such a way that a focal spot is formed at a desired position on the anode ring with said spot moving continuously about the anode ring along an arc. After the focal spot has traveled through all desired positions, the first electron source is switched off again by increasing the negative voltage on its hollow cathode segments to several kilovolts and, simultaneously or immediately thereafter, a second neighboring electron source is switched on by proceeding in the manner used for the first source. The starting position of the focal point emanating from the second source is approximately that of the ending position of the focal spot emanating from the first source. After the focal spot of the second source has reached its desired end position, said source is switched off as described, and a third source is correspondingly switched on. The procedure is then successively repeated for all sources in the electron ring until the focal spot has traveled through an arc of at least 180° preferentially 360°.

Clearly, variations of this first described operation mode are possible. For example, not all electron sources must be operated, that is to say, the filaments of several, by way of example, half of all sources could be unheated.

In the second operation mode, which has a discontinuous focal spot motion, one view angle is generated for each focal spot position by reading out the detector elements which lie within the field of view. This read out procedure can be completed in, by way of example, approximately 20 microseconds. During this time, the focal spot is steered upon the anode through or about its average position, said position defining the corresponding view angle. The next sequential view angle can be far removed spatially from the previous one. A one slice analysis of a sequence of angle measurements with discontinuous focal spot positions yields an image whose spatial resolution is comparable to that achieved in the first operation mode with continuous focal spot motion and two slice analysis. In the second operating mode with discontinuous motion of the focal spot and one slice analysis, the minimum time resolution for the image is, however, dependent upon the number of view angles used in the analysis, whereby, the time resolution increases approximately linearly with the number of view angles and is not, therefore, a fixed fraction of the scan time. By way of example, it is possible to effect an image with 50 view angles with a time resolution of approximately 1 ms and an image with 250 view angles would have a time resolution of approximately, by way of example, 5 ms. In certain special cases it is possible to switch in several electron sources at the same time.

Further advantages can be derived from the description and the accompanying drawings. Clearly the characterizing features mentioned above and the described below are applicable not only in the corresponding combination given but also in other combinations or by themselves without departing from the framework of the current invention.

Embodiments of the invention are represented in the drawings and are described in the following description. Shown are:

BRIEF DESCRIPTION OF THE DRAWING

FIG. 3: An enlarged cross section through the gantry with the devices for production and detection of the fan beam, FIG. 4: The detector ring viewed from the center of the anode and detector ring, FIG. 5: A qualitative representation of the principal of production of the fan beam, FIG. 7A: A possible operation mode of a tomograph according to the invention.

FIG. 7B: Another possible operation mode of a tomograph according to the invention.

DETAILED DESCRIPTION OF THE PREFERRED EMBODIMENTS

Figure 1:
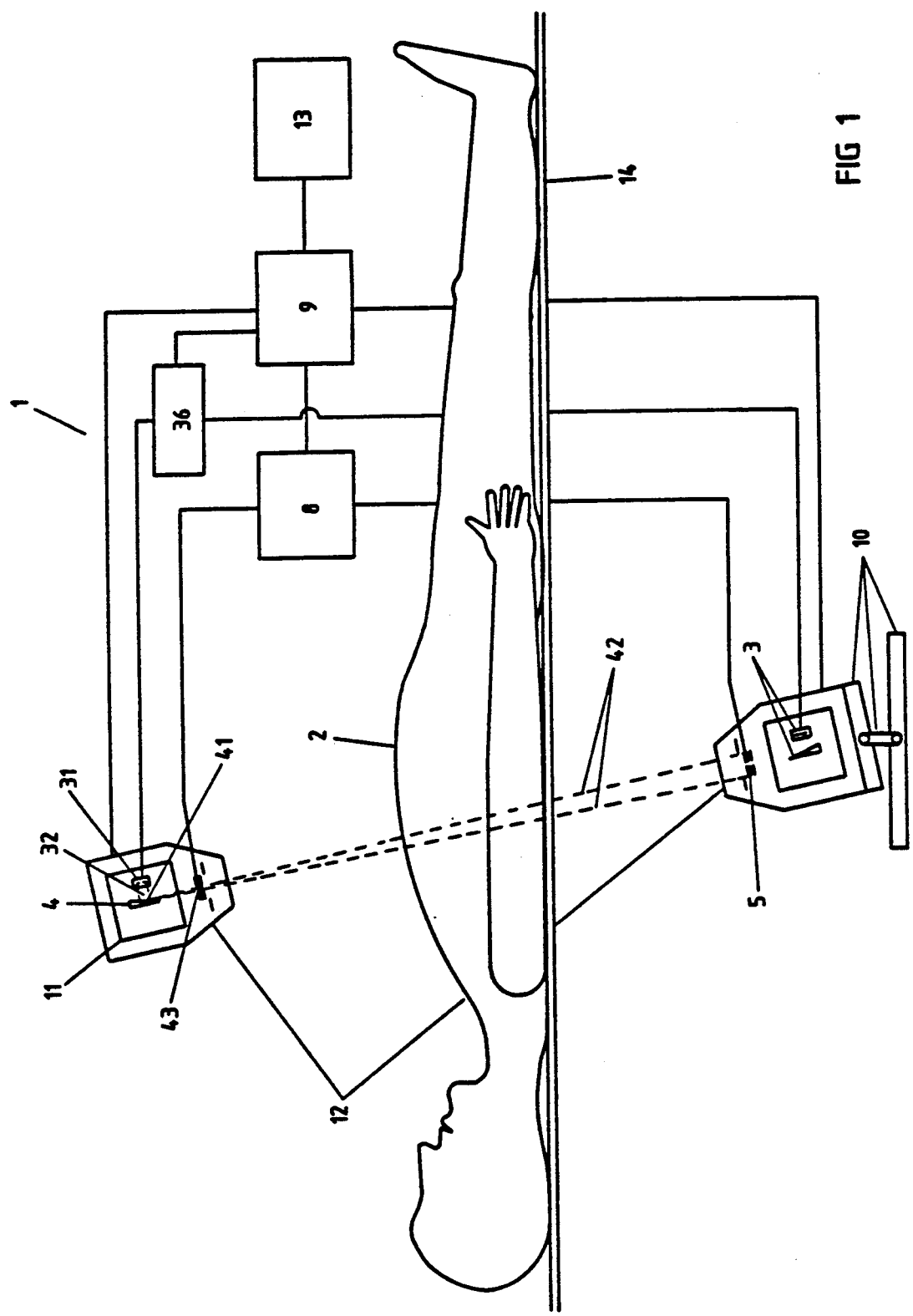
FIG. 1: A schematic representation of a computer tomography scanner according to the invention.

In particular, FIG. 1 shows a overview of the X-ray computer tomography scanner (1) according to the invention. An X-ray source (3) which is comprised of a plurality of electron sources (31) and an anode ring (4) which are located within a common vacuum housing (11) produces X-ray radiation at positions of the focal spots (41) stemming from collisions between electrons from the electron source (31) in the electron beam (32) with the anode ring (4). The X-ray radiation emanating from the position of the focal spot (41) is collimated into a fan beam (42) using a beam collimator (43) before passing through the object (2) being studied, and this object can be brought to a desired position within the opening of the gantry (12) through the travel provided by a moving support structure (14). After the fan beam (42) has penetrated through the object (2) it is detected in a detector ring (5). The X-ray intensity transmitted through the object (2) is converted into electrical signals by detector elements of the detector ring (5) the size of which is largely linearly proportional to the X-ray intensity incident upon the corresponding detector element. The signals are then digitized in an analog-digital converter (8) and transferred to a computer (9). The computer controls and manages the scan functions and can be configured as either a unified computing entity or as a network of coupled or uncoupled computers. The scan functions mentioned include among other things, means (36) to control the electron sources (31). The computer reconstructs an image slice through the object using data taken by the detector elements of the detector ring (5). This image slice is, by way of example, displayed on a picture screen (13). A tilt mechanism (10) is provided for in order to tilt the gantry (12) over a certain angular region with respect to the vertical.

Figure 2B:
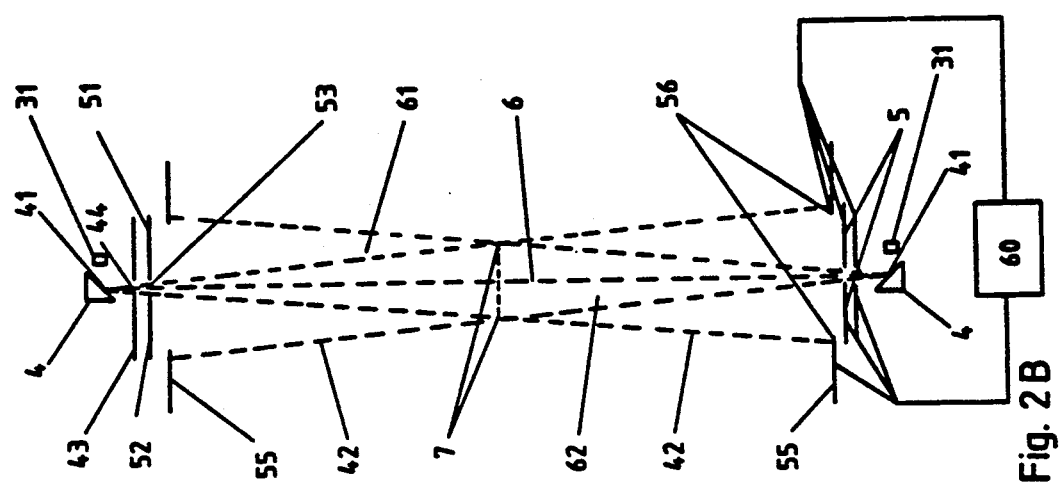
FIG. 2B: A side view of the system geometry.
Figure 2A:
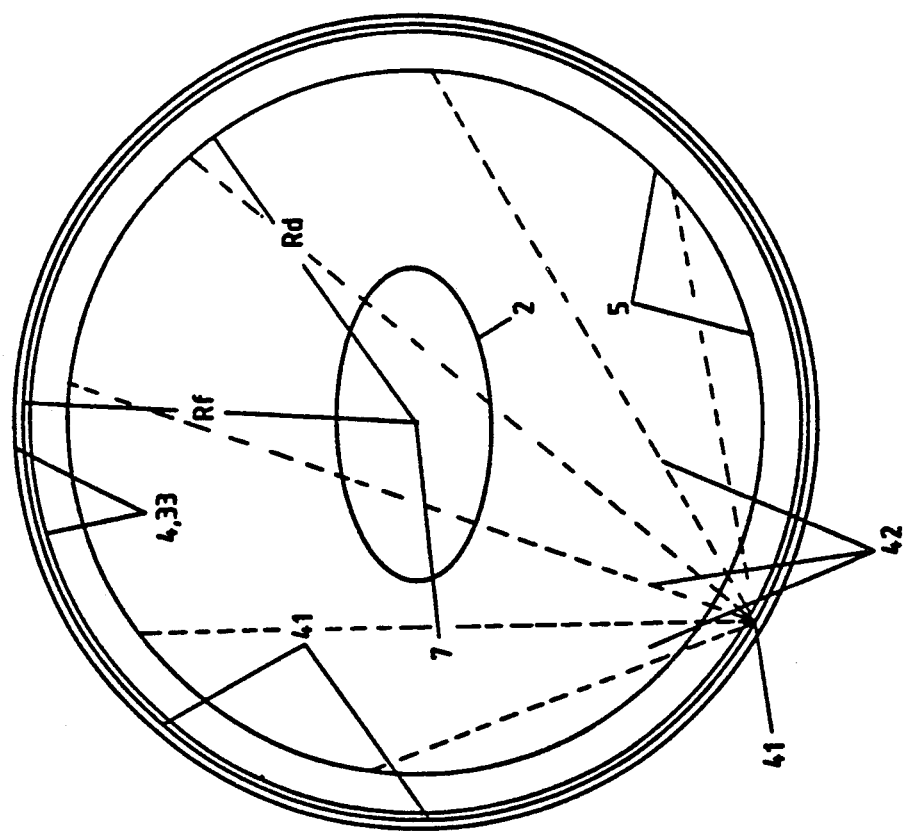
FIG. 2A: A front view of the system geometry.

FIG. 2A and FIG. 2B show the fundamental geometry of a preferred version of the invention. FIG. 2B shows a front view and FIG. 2B a cross sectional or a side view. The possible positions of the focal spot (41) on the anode ring (4) describe a circle of radius Rf which is concentric with the detector ring (5) of radius Rd whereby Rf is larger than Rd. A plurality of electron sources (31) are arranged on an electron source ring (33) which is located in proximity to the anode ring (4). The fan beam (42) originates at one of the several positions of the focal spot (41) on the anode ring (4). An object (2) is located near the center (7) of the anode and detector ring. X-ray radiation emanating from the focal spot (41) is collimated into a fan beam (42) with a beam collimator (43) which is located between the anode (4) and detector rings (5) by passing through the beam collimator gap (44). The fan beam (42) passes through the detector ring gap (53), the object (2), and is further collimated through the detector collimator gap (56) of the detector collimator (55), before it is detected in the detector elements of the detector ring (5). As the focal spot (41) moves about the anode ring (4) the fan beam (42) cuts through the object (2) in an approximately flat slice (6) which consists of two neighboring partial slices (61, 62) whereby, one partial slice (61) is formed from the part of the fan beam intersecting one detector partial ring (51) and the other partial slice (62) from the portion illuminating the other detector partial ring (52). Means (60) are available for varying the thickness of this slice (6) or partial slice (61, 62) respectively, in that one adjusts the width of the beam collimator gap (44) the detector ring gap (53) and the detector collimator gap (56).

FIG. 3 shows a cross section through a portion of the gantry (12). Means (36) are provided for controlling the electron sources (31) such that these means (36) are capable of applying time and position dependent voltages on the surface of the hollow cathodes (35). By varying these voltages, the electron beam (32) leaving the filament (34) can be switched on and switched off as well as focused and steered. The electron beam (32) collides with the anode ring (4) at the focal point position (41) and effects the emission of X-ray radiation. The electron sources (31) and the anode ring (4) are located in a common vacuum housing (11). The X-ray beam emitted from the focal spot (41) is collimated by means of the beam collimator (43) into a fan beam (42) which passes through the detector ring gap (53) separating the two detector partial rings (51, 52) of the detector ring (5). The detector collimator (55) limits the effective width of the fan beam (42) which has passed through the object at the location opposite to the focal spot position on the anode ring (4).

FIG. 4 gives a view of a part of the detector ring (5) as seen from the center of the anode (4) or detector ring (5) respectively. The detector ring (5) consists of two detector partial rings (51, 52) which are separated by a detector partial ring gap (53). Each partial detector ring (51, 52) includes a plurality of individual detectors or detector elements respectively (54). In an preferred embodiment of the invention, there are 1200 such detector elements (54) in each of the two detector partial rings (51, 52), that is to say, a total of 2400 detector elements (54). The signal from each detector element (54) is digitized in an analog-digital converter and the data derived thereby is utilized by a computer to construct image slices through the object. It is furthermore particularly advantageous when the two detector partial rings (51, 52) are rotated with respect to each other by an arc length D/2 which corresponds to the detector ring circumference divided by two times the number of detector elements (54) per detector partial ring (51 or 52).

FIG. 5 qualitatively describes the principals of function of the electron sources (31). FIG. 5 shows a section of the anode (4) and the electron source ring (33) as viewed from the center of the anode (4) or detector ring. The electron source ring (33) consists of an array of adjacent electron sources (31) located in close proximity to the anode ring (4). FIG. 5 shows explicitly three electron source rings (31). In a preferred embodiment of the invention, each electron source (31) consists of a hollow cathode (35) and a heatable filament (34). The hollow cathode (35) is subdivided into two segments which are electrically insulated from each other. The anode ring (4) is at an electrical potential of +130 kV relative to the filaments (34), whereby the filaments (34) are preferentially at ground potential. The shape of the hollow cathodes (35) and their separation from the anode ring (4) are chosen such that the corresponding electrons emitted from the filament (34) are focused into an electron beam (32) and accelerated towards the focal spot (41) on the anode ring (4). By the application of suitable negative voltages of up to several kV (relative to the filament) of variable strength on one or more of the hollow cathode segments (35a,b) of an electron source (31), its corresponding electron beam (32) can be switched on and switched off and/or focused and steered. The position of the focal spot (41) of the electron beam (32) of a given electron source (31) on the anode ring (4) is determined by the voltage which is applied to the two segments (35a,b) of the hollow cathode (35) of the electron source (31). The electrical field lines (39) corresponding to the voltage condition with which the electron source (31) is switched off, that is to say, there are effectively no electrons emanating from the filament (34), are qualitatively represented for one of the electron sources (31) in FIG. 5. During a scan, the voltage on the anode ring (4) is held constant and the potentials on the hollow cathode segments (35a,b) are varied. Means (49) are provided for supporting the anode ring (4) and for isolating it with respect to ground, as well as means (48) for applying high voltage (preferentially +130 kV) to it. Possible variations of these embodiments have the voltage level of the anode ring (4), the hollow cathode (35), and the filaments (34) shifted by a constant voltage amount relative to ground.

Figure 6:
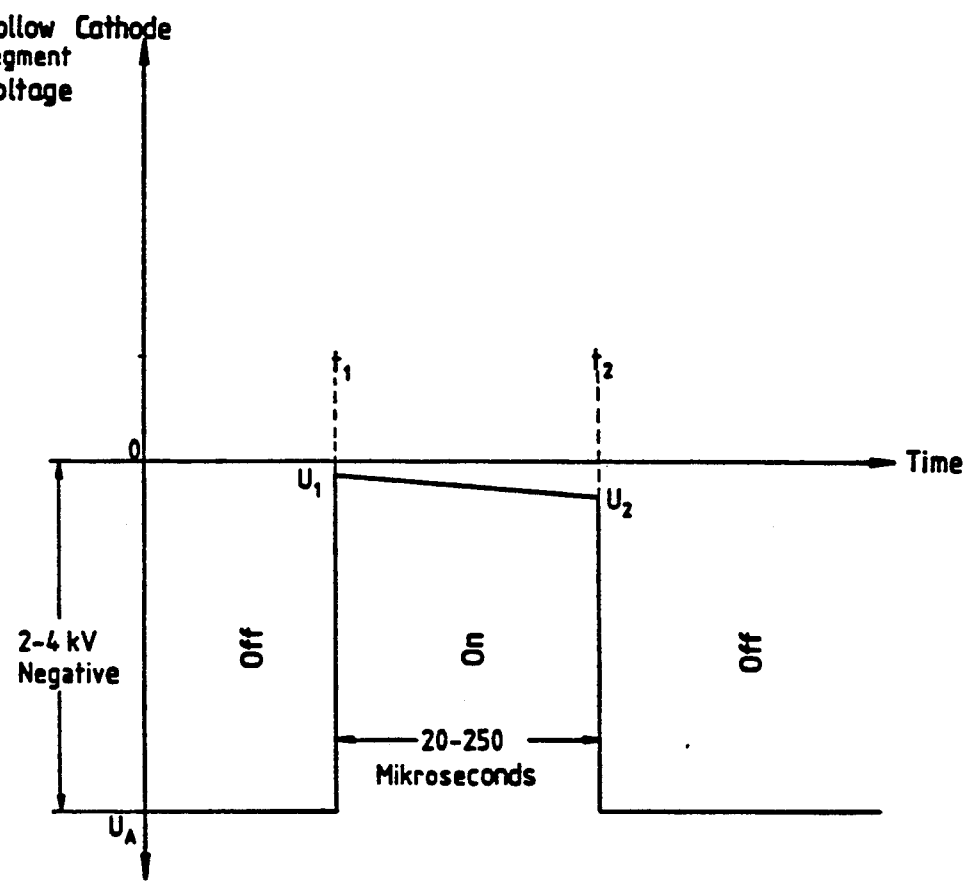
FIG. 6: A diagram of the time dependence of the high voltage on a hollow cathode segment.

FIG. 6 is a schematic representation of the time dependence of the voltage applied to a segment (35a or 35b) of a hollow cathode (35) in a preferred embodiment of the invention with two segments (35a, b) per hollow cathode configuration as described in FIG. 5. A negative voltage UA of several kV is initially present on both segments of the hollow cathode. Thereby, the electron source is switched off. At time t1 the voltage on the segment shown is reduced to approximately ground potential. Preferentially, this also occurs on the other segment of the hollow cathode, whereby a small voltage deviation U1 from ground potential can remain, which is different for each of the two segments. In the time interval between t1 and t2, the electron source is switched on. This time interval corresponds to, in general, 20 to 250 microseconds. During this time, the residual voltages on the hollow cathode segments are, preferentially, varied oppositely in order to steer the emitted electron beam. At time t2, the residual voltage U2 on the segment shown is again increased to the negative voltage UA which, in general, also takes place at the same time in the neighboring segment of the hollow cathode. Thereby, the electron source is switched off again.

FIGS. 7A and 7B describe possible operation modes of a X-ray computer tomography scanner according to the invention. In FIG. 7A, a first operation mode is indicated whereby each detector element (54) produces one view angle (21) per scan. In FIG. 7A, a detector element (54) is located at position A on the detector ring (5) and detects X-ray radiation from the focal spot (41) while the focal spot (41) is continuously moving about the anode ring (4) from position B to position C. When the focal spot is located in the positions B and C the connecting lines AB and AC are tangent to the circle (20) which borders the field of view. This circle (20) of the field of view is concentric with the detector (5) and anode rings (4) respectively, and the object (2) is located in the field of view (20). The detector elements (54) at the position A is read out 1200 times in equidistant time intervals while the focal spot (41) moves from B to C and a view angle (21) is thereby produced which is composed of 1200 equidistant measured values of the X-ray intensity passing through the field of view (20).

In the second operation mode described in FIG. 7B, a view angle (21) is produced for a position A of the focal spot (41) on the anode ring (4) in that all detector elements (54) between the points B and C on the detector ring (5) are read out. These detector elements (54) have measured the X-ray intensity emanating from the focal spot (41) which has passed through the field of view (20) with the object (2). In this operation mode, the focal spot (41) can jump discontinuously from one spot on the anode ring (4) to another, with a view angle (21) being produced for each position.

We claim:

1. In an X-ray computer tomography system for generating an image of an object, the system having a plurality of stationary electron sources, each of the plurality of electron sources having means for emitting electrons and being arranged in proximity to a stationary anode, means for applying an electric potential between each of the plurality of electron sources and the anode to accelerate the electrons from each of the plurality of electron sources to the anode so that the electrons collide with the anode at focal spots and generate X-ray radiation, a detector responsive to the X-ray radiation for generating image signals, and means responsive to the image signals for generating an image, the improvement comprising means located proximal to the electron emitting means in each of the plurality of electron sources for directing electrons moving from the electron emitting means to the anode and means for generating a steering field between the directing means and the electron emitting means so that the focal spots are swept over predetermined portions of the anode before any substantial acceleration of the electrons takes place.

2. In an X-ray computer tomography system, the improvement according to claim 1 wherein the electron emitting means comprises a filament and the direction means comprises a partially surrounding cathode the partially surrounding cathode having a surface shaped to focus electrons emitted from the filament into an electron beam which impinges on the anode at the focal spot and the steering field generating means comprises means for applying a variable voltage between the filament and the partially surrounding cathode.

3. In an X-ray computer tomography system, the improvement according to claim 2 wherein the means for applying a variable voltage comprises means for applying spatially variable voltages between the filament and the surface of the partially surrounding cathode.

4. In an X-ray computer tomography system, the improvement according to claim 2 wherein the partially surrounding cathode is subdivided into a plurality of segments which are mutually electrically insulated from each other and wherein means are provided for applying differing voltages to each of the plurality of partially surrounding cathode segments so that the electron beam is swept across the anode.

5. An X-ray computer tomography system for generating an image of an object comprising:
a stationary ring-shaped anode;
a plurality of stationary electron sources, each of the plurality of electron sources being located in proximity to the ring-shaped anode and having means for emitting electrons;
means for controlling each of the plurality of electron sources to generate electrons in a predetermined time sequence;
means for applying an electric potential between each of the electron sources and the anode to accelerate the electrons from each of the plurality of electron sources to the anode so that the electrons collide with the anode at a plurality of focal spots to generate X-ray radiation;
means located proximal to the electron emitting means in each of the plurality of electron sources for directing electrons moving from the electron emitting means to the anode and means for generating a steering field between the directing means and the electron emitting means so that the focal spots are swept over predetermined portions of the anode before any substantial acceleration of the electrons takes place; and
a detector responsive to the X-ray radiation for generating the image signals.

6. An X-ray computer tomography system according to claim 5 wherein each of the plurality of electron emitting means comprises a filament and the directing means comprises a plurality of cathodes, each of the plurality of cathodes comprising a first cathode portion partially surrounding one of the plurality of filaments and a second cathode portion partially surrounding the one filament and electrically insulated from the first cathode portion, and wherein the means for generating the steering field comprises first means for applying an electric potential to the first cathode portion and second means for applying an electric potential to the second cathode portion.

7. An X-ray computer tomography system according to claim 6 wherein the first cathode portion and the second cathode portion are substantially identical in shape and form a hollow when placed together in which hollow the one filament is located and the first cathode portion and the second cathode portion are shaped to focus electrons emitted from the one filament into an electron beam which impinges on the anode at one of the plurality of focal spots and the first applying means and the second applying means apply electric potentials to the first and second cathode portions so that the electron beam is swept across the anode.

8. An X-ray computer tomography system according to claim 5 wherein the ring-shaped anode is planar and the detector comprises two detector rings located coaxially on either side of the planar anode.

9. An X-ray computer tomography system according to claim 5 wherein the plurality of electron sources are located in a ring positioned coaxially with the anode ring.

10. An X-ray computer tomography system according to claim 5 wherein the plurality of electron sources are located in a ring positioned coaxially with the anode ring.

11. An X-ray computer tomography system for the production of image slices through an object, the system comprising:
a plurality of stationary electron sources arranged in a plant ring, each of the plurality of electron sources comprising a filament, a partially surrounding cathode, and means for applying voltages to the partially surrounding cathode;

a stationary ring-shaped planar anode positioned coaxially with and in proximity to the electron source ring;

means for accelerating electrons emitted from each of the plurality of electron sources towards the anode ring, whereby the electrons from each of the plurality of electron sources form an electron beam which collides with the anode ring at a focal spot to generate X-ray radiation;

means for collimating the X-ray radiation emanating from the focal spot into an X-ray fan beam;

a ring-shaped detector positioned coaxially to the electron source ring; and means for controlling the voltage applying means in each of the plurality of electron sources to apply a temporally and spatially variable voltage to the partially surrounding cathode so that the plurality of electron sources emit electron beams in a predetermined time sequence and so that the focal spots produced by the electron beams on the anode ring are each electromagnetically swept over a predetermined portion of the anode ring.

12. An X-ray computer tomography system according to claim 11, wherein the detector ring is comprised of two parallel detector partial rings positioned substantially coplanar with the anode ring plane and located on either side of the anode ring so that a ring-shaped detector gap is formed between the detector partial rings through which X-ray radiation emanating from a focal spot passes.

13. An X-ray computer tomography system according to claim 12, wherein the anode ring and the detector partial rings are positioned so that the geometrical relationship:

$$Rd/Rf = (wd-g)/(wd+g)$$

is approximately satisfied, in which g is the width of the detector ring gap, wd is the width of an X-ray radiation fan beam at the position of the detector ring opposite to an electron beam focal spot which generated the X-ray radiation, Rd is the distance from the detector ring to the detector ring center and Rf is the distance from the focal spot to the anode ring center.

14. An X-ray computer tomography system according to claim 12, further comprising a pair of ring-shaped beam collimators located coaxially with the electron source ring and positioned on either side of the anode ring to form a beam collimator gap between the beam collimators and means for adjusting the separation of the detector partial rings and the separation of the beam collimators to change the thickness of a scan slice through the object.

15. An X-ray computer tomography system according to claim 12, wherein each of the detector partial rings is comprised of a predetermined plurality of detector elements and the detector partial rings are rotated with respect to each other so that detector elements of the two partial rings are displaced with respect to each other by a distance of one-half the width of a detector element.

16. An X-ray computer tomography system according to claim 11 wherein each partially surrounding cathode exhibits at least two electrically insulated cathode segments and wherein each of the plurality of electron sources further comprises means for applying a variable voltage between the filament and the cathode segments in order to control the intensity of the electron beam emitted from each electron source.

17. A method for operating an X-ray computer tomography system having a stationary anode, a plurality of stationary electron sources in proximity to the anode each of the plurality of electron sources having means for emitting electrons and being controllable to generate an electron beam, means for applying an electric potential between each of the electron sources and the anode to cause the electron beam generated by each source to accelerate and collide with the anode at a focal spot and to generate X-ray radiation, the method comprising the steps of:

A. controlling each of the plurality of electron sources so that none of the plurality of electron sources generates an electron beam;

B. selecting one of said plurality of electron sources;

C. controlling the selected electron source to generate an electron beam to form a focal spot;

D. generating a steering field in the vicinity of the electron emitting means in the selected electron source to deflect the electrons before substantial acceleration of the electrons takes place in order to move the focal spot formed in step C over the predetermined portion of the anode ring;

E. controlling the selected electron source to stop generation of the electron beam;

F. selecting another one of the plurality of electron sources and

G. repeating steps C through F until a predetermined number of the plurality of electron sources have been selected.

18. A method for operating an X-ray computer tomography system according to claim 17 wherein the focal spot moves over an arc of at least 180 degrees.

19. A method for operating an X-ray computer tomography system according to claim 17 wherein the X-ray computer tomography system has a detector ring consisting of two partial detector rings and the method further comprises the steps of:

H. detecting X-ray radiation generated from the focal spot on the anode with the two partial detector rings after the X-ray radiation has passed through an object; and I. constructing two separate images of two neighboring partial slices through the object from the X-ray radiation detected in step H.

20. A method for operating an X-ray computer tomography system according to claim 17 wherein the X-ray computer tomography system has a detector ring consisting of two partial detector rings and the method further comprises the steps of:

J. detecting X-ray radiation generated from the focal spot on the anode with the two partial detector rings after the X-ray radiation has passed through an object; and K. constructing a single image of a slice through the object from the X-ray radiation detected in step J.

21. In an X-ray computer tomography system for generating an image of an object, the system having a plurality of stationary electron sources arranged in proximity to a stationary anode, means for applying an electric potential between the electron sources and the anode to accelerate the electrons from the electron sources to the anode so that the electrons collide with the anode at focal spots and generate X-ray radiation, a detector responsive to the X-ray radiation for generating image signals, and means responsive to the image signals for generating an image, the improvement wherein each of the plurality of electron sources comprises a filament and a partially surrounding cathode, said partially surrounding cathode having a surface shaped to focus electrons emitted from the filament into an electron beam which impinges on the anode at the focal spot and wherein the improvement further comprises means for electromagnetically sweeping the focal spots over predetermined portions of the anode comprising means for applying spatially variable voltages between the filament and the surface of the partially surrounding cathode.

22. An X-ray computer tomography system for generating an image of an object comprising:
 a stationary ring-shaped anode;
 a plurality of stationary electron sources in proximity to the ring-shaped anode, each of the plurality of electron sources comprising a filament;
 means for controlling each of the plurality of electron sources to generate electrons in a predetermined time sequence;
 means for applying an electric potential between each of the electron sources and the anode to accelerate the electrons from each of the plurality of electron sources to the anode so that the electrons collide with the anode at a plurality of focal spots to generate X-ray radiation;
 means for electromagnetically sweeping the focal spots over predetermined portions of the anode comprising a plurality of cathodes, each of the plurality of cathodes comprising a first cathode portion partially surrounding one of the plurality of filaments and a second cathode portion partially surrounding the one filament and electrically insulated from the first cathode portion, first means for applying an electric potential to the first cathode portion and second means for applying an electric potential to the second cathode portion; and
 a detector responsive to the X-ray radiation for generating the image signals.

23. The X-ray computer tomography system according to claim 22 wherein the first cathode portion and the second cathode portion are substantially identical in shape and form a hollow when placed together in which the one filament is located and wherein the first cathode portion and the second cathode portion are shaped to focus electrons emitted from the one filament into an electron beam which impinges on one anode at one of the plurality of focal spots and wherein the first applying means and the second applying means apply electric potentials to the first and second cathode portions so that the electron beam is swept across the anode.

24. An X-ray computer tomography system for the production of image slices through an object, the system comprising:
 a plurality of stationary electron sources arranged in a planar ring, each of the plurality of electron sources comprising a filament, a partially surrounding cathode having at least two electrically insulated cathode segments, means for applying voltages to the partially surrounding cathode and means for applying a variable voltage between the filament and each of the cathode segments in order to control the intensity of the electron beam emitted from each electron source;
 a stationary ring-shaped planar anode positioned coaxially with and in proximity to the electron source ring;
 means for accelerating electrons emitted from each of the plurality of electron sources towards the anode ring, whereby the electrons from each of the plurality of electron sources form an electron beam which collides with the anode ring at a focal spot to generate X-ray radiation;
 means for collimating the X-ray radiation emanating from the focal spot into an X-ray fan beam;
 a ring-shaped detector positioned coaxially to the electron source ring; and
 means for controlling the voltage applying means in each of the plurality of electron sources so that the plurality of electron sources emit electron beams in a predetermined time sequence and so that the focal spots produced by the electron beams on the anode ring are each electromagnetically swept over a predetermined portion of the anode ring.

25. In an X-ray computer tomography system for generating an image of an object, the system having a plurality of stationary electron sources arranged in proximity to a stationary anode, means for applying an electric potential between each of plurality of electron sources and the anode to accelerate the electrons from each of the plurality of electron sources tot he anode so that the electrons collide with the anode at focal spots and generate X-ray radiation, a detector responsive to the X-ray radiation for generating image signals, and means responsive to the image signals for generating an image, the improvement wherein each of the plurality of electron sources comprises:
 a filament;
 a cathode having a plurality of physical segments shaped and located with respect tot he filament to focus electrons emitted from the filament into an electron beam; and
 sweeping means for applying variable voltages between the filament and each of the plurality of cathode segments in order to sweep the electron beam across the anode.

26. An X-ray computer tomography system for generating an image of an object comprising:
 a stationary ring-shaped anode;
 a plurality of stationary electron sources located in proximity to the ring-shaped anode, each of the plurality of electron sources comprising a filament, a first cathode portion partially surrounding the filament and a second cathode portion partially surrounding the filament and electrically insulated from the first cathode portion;
 means for controlling each of the plurality of electron sources to generate electrons in a predetermined time sequence;
 means for applying an electric potential between each of the electron sources and the anode to accelerate the electrons from each of the plurality of electron sources to the anode so that the electrons collide with the anode at a plurality of focal spots to generate X-ray radiation;
 first means for applying an electric potential to the first cathode portion of each of said plurality of electron sources and second means for applying an electric potential to the second cathode portion of each of said plurality of electron sources in order to electromagnetically sweep the focal spots over predetermined portions of the anode; and a detector responsive to the X-ray radiation for generating the image signals.

27. The X-ray computer tomography system according to claim 26 wherein the first cathode portion and the second cathode portion are substantially identical in shape and are located with respect to the filament to focus electrons emitted from the filament into an electron beam.

28. An X-ray computer tomography system according to claim 26 wherein the ring-shaped anode is planar and the detector comprises two detector rings located coaxially on either side of the planar anode.

29. A method for operating an X-ray computer tomography system having a stationary anode, a plurality of stationary electron sources in proximity to the anode each of which is controllable to generate an electron beam and each of which has a filament, a first cathode portion partially surrounding the filament and a second cathode portion partially surrounding the filament and electrically insulated from the first cathode portion, means for applying an electric potential between each of the electron sources and the anode to cause the electron beam generated by each source to collide with the anode at a focal spot and to generate X-ray radiation, means for electromagnetically sweeping each focal spot over a predetermined portion of the anode, the method comprising the steps of:
  A. controlling each of the plurality of electron sources so that none of the plurality of electron sources generates an electron beam;
  B. selecting one of said plurality of electron sources;
  C. controlling the selected electron source to generate an electron beam to form a focal spot;
  D. applying a temporally and spatially variable voltage to the first cathode portion and the second cathode portion in the electron source selected in step B in order to move the focal spot formed in step C over the predetermined portion of the anode ring;
  E. controlling the selected electron source to stop generation of the electron beam;
  F. selecting another one of the plurality of electron sources and
  G. repeating steps C through F until a predetermined number of the plurality of electron sources have been selected.

30. An X-ray computer tomography system for the production of image slices through an object, the system comprising:
  a plurality of stationary electron sources arranged in a planar ring, each of the plurality of electron sources comprising a filament, a partially surrounding cathode, and means for applying voltages to the partially surrounding cathode;
  a stationary ring-shaped planar anode positioned coaxially with and in proximity to the electron source ring;
  means for accelerating electrons emitted from each of the plurality of electron sources towards the anode ring, whereby the electrons from each of the plurality of electron sources form an electron beam which collides with the anode ring at a focal spot to generate X-ray radiation;
  means for collimating the X-ray radiation emanating from the focal spot into an X-ray fan beam;
  a ring-shaped detector positioned coaxially to the electron source ring; and
  means for controlling the voltage applying means in each of the plurality of electron sources to apply a temporally and spatially varying voltage to the partially surrounding cathode in each of the plurality of electron sources so that the plurality of electron sources emit electron beams in a predetermined time sequence and so that the focal spots produced by the electron beams on the anode ring are each electromagnetically swept over a predetermined portion of the anode ring.

31. An X-ray computer tomography system according to claim 30, wherein the detector ring is comprised of two parallel detector partial rings positioned substantially coplanar with the anode ring so that a ring-shaped detector gap is formed between the detector partial rings through which X-ray radiation emanating from a focal spot passes.

32. An X-ray computer tomography system according to claim 31, wherein the anode ring and the detector partial rings are positioned so that the geometrical relationship:

$$Rd/Rf=(wd-g)/(wd+g)$$

is approximately satisfied, in which g is the width of the detector ring gap, wd is the width of an X-ray radiation fan beam at the position of the detector ring opposite to an electron beam focal spot which generated the X-ray radiation, Rd is the distance from the detector ring to the detector ring center and Rf is the distance from the focal spot to the anode ring center.

33. An X-ray computer tomography system according to claim 31, further comprising a pair of ring-shaped beam collimators located coaxially with the electron source ring and positioned on either side of the anode ring to form a beam collimator gap between the beam collimators and means for adjusting the separation of the detector partial rings and the separation of the beam collimators to change the thickness of a scan slice through the object.

34. An X-ray computer tomography system according to claim 31, wherein each of the detector partial rings is comprised of a predetermined plurality of detector elements and the detector partial rings are rotated with respect to each other so that detector elements of the two partial rings are displaced with respect to each other by a distance of one-half the width of a detector element.

35. An X-ray computer tomography system according to claim 31, wherein each partially surrounding cathode exhibits at least two electrically insulated cathode segments and wherein each of the plurality of electron sources further comprises means for applying a variable voltage between the filament and the cathode segments in order to control the intensity of the electron beam emitted from each electron source.

* * * * *